(12) United States Patent
Bar-Tal et al.

(10) Patent No.: US 10,517,670 B2
(45) Date of Patent: Dec. 31, 2019

(54) ESTIMATION OF LESION SIZE

(71) Applicants: BIOSENSE WEBSTER (ISRAEL) LTD., Yokneam (IL); University of Oklahoma Health Sciences Center, Oklahoma City, OK (US)

(72) Inventors: Meir Bar-Tal, Haifa (IL); Erez Silberschein, Tel Aviv (IL); Assaf Rubissa, Misgav (IL); Garth Francis Constantine, Murrieta, CA (US); Hiroshi Nakagawa, Edmond, OK (US)

(73) Assignees: Biosense Webster (Israel) Ltd., Yokneam (IL); University of Oklahoma Health Sciences Center, Oklahoma City, OK (US)

( * ) Notice: Subject to any disclaimer, the term of this patent is extended or adjusted under 35 U.S.C. 154(b) by 640 days.

(21) Appl. No.: 15/177,826

(22) Filed: Jun. 9, 2016

(65) Prior Publication Data

US 2017/0014181 A1    Jan. 19, 2017

Related U.S. Application Data

(60) Provisional application No. 62/193,179, filed on Jul. 16, 2015.

(51) Int. Cl.
*A61B 18/14* (2006.01)
*A61B 18/00* (2006.01)

(52) U.S. Cl.
CPC ............ *A61B 18/1492* (2013.01); *A61B 2018/00351* (2013.01); *A61B 2018/00577* (2013.01);
(Continued)

(58) Field of Classification Search
CPC ............ A61B 18/1233; A61B 18/1492; A61B 2018/00351; A61B 2018/00577;
(Continued)

(56) References Cited

U.S. PATENT DOCUMENTS 6,936,047 B2    8/2005   Nasab et al.
7,001,383 B2    2/2006   Keidar
(Continued)

FOREIGN PATENT DOCUMENTS

EP    2 248 480 A1    11/2010
EP    2338428 A1      6/2011
(Continued)

OTHER PUBLICATIONS

Bhavaraju et al., "Measurement of Directional Thermal Properties of Biomaterials", IEEE Transactions on Biomedical Engineering, Feb. 2001, vol. 48(2), pp. 261-267.
(Continued)

*Primary Examiner* — Lee S Cohen
*Assistant Examiner* — Tigist S Demie
(74) *Attorney, Agent, or Firm* — Lewis Roca Rothgerber Christie LLP

(57) ABSTRACT

A method, consisting of ablating tissue for a time period, measuring a contact force applied during the time period, and measuring a power used during the time period. The method further includes ceasing ablating the tissue when a desired size of a lesion produced in the tissue, as estimated using an integral over the time period of a product of the contact force raised to a first non-unity exponent and the power raised to a second non-unity exponent, is reached.

14 Claims, 10 Drawing Sheets

(52) U.S. Cl.
CPC ............... *A61B 2018/00648* (2013.01); *A61B 2018/00708* (2013.01); *A61B 2018/00738* (2013.01); *A61B 2018/00779* (2013.01); *A61B 2018/00827* (2013.01)

(58) Field of Classification Search
CPC ........... A61B 2018/00648; A61B 2018/00678; A61B 2018/00708; A61B 2018/00738; A61B 2018/00779; A61B 2018/00827; A61B 2018/00886; A61B 2018/00988; A61B 2090/065
See application file for complete search history.

(56) References Cited

U.S. PATENT DOCUMENTS

| | | | |
|---|---|---|---|
| 7,306,593 | B2 | 12/2007 | Keidar et al. |
| 8,641,705 | B2 | 2/2014 | Leo et al. |
| 9,237,920 | B2 | 1/2016 | Leo et al. |
| 2012/0209260 | A1* | 8/2012 | Lambert ............ A61B 18/1492 606/41 |

FOREIGN PATENT DOCUMENTS

| | | |
|---|---|---|
| EP | 2 719 351 A1 | 4/2014 |
| WO | WO 2011/034925 A1 | 3/2011 |
| WO | WO 2012/092275 A1 | 7/2012 |

OTHER PUBLICATIONS

Bhavaraju et al., "Thermophysical Properties of Swine Myocardium", Int'l J. of Thermophysics, Nov. 2, 1999, vol. 20(2), pp. 665-676.
Bhavaraju, Heat Transfer Modeling during Radiofrequency Cardiac Ablation in Swine Myocardium, PhD Dissertation, Univ. of Texas-Austin, Mar. 2000, pp. 1-138.
Cao et al., "Myocardial Temperature Monitoring during RF Ablation", PACE, Apr. 1999 (Part II), vol. 22, p. 846.
Cao et al., "Using Electrical Impedance to Predict Catheter-Endocardial Contact During RF Cardiac Ablation", IEEE Transactions on Biomedical Engineering, Mar. 2002, vol. 49(3), pp. 247-253.
Cao et al., "Flow Effect on Lesion Formation in RF Cardiac Catheter Ablation", IEEE Transactions on Biomedical Engineering, Apr. 2001, vol. 48(4), pp. 425-433.
Cao et al., "FEM Analysis of Predicting Electrode—Myocardium Contact From RF Cardiac Catheter Ablation System Impedance", IEEE Transactions on Biomedical Engineering, Jun. 2002, vol. 49(6), pp. 520-526.
Cao et al.,"Temperature Measurement within Myocardium During In Vitro RF Catheter Ablation", IEEE Transactions on Biomedical Engineering, Nov. 2000, vol. 47(11), pp. 1518-1524.
Cao et al., "Validation of RF Catheter Ablation Models Using Basket Electrodes" Proceedings—19th Int'l Conference—IEEE/EMBS, Oct. 30-Nov. 2, 1997 Chicago, IL, USA, pp. 395-398.
Cao, "Measuring Contact Area and Temperature During Radio-Frequency Cardiac Catheter Ablation", PhD Dissertation (5.5 MB), Univ. of Wisconsin-Madison, 2001, pp. 1-179.
Cao, "Preliminary Exam: Myocardial temperature monitoring during RF catheter ablation—in vitro and in vivo", Power Point Presentation (1.1 MB), Apr. 1, 2000.
Choy et al., "Mechanical compliance of the endocardium", J. of Biomechanics, 2002, vol. 35, pp. 1671-1676.
Choy et al., "Preserving Mechanical Compliance of the Endocardium Using Wisconsin Solution", J. Biomech, submitted 2001.
Dos Santos et al., "An instrument to measure the heat convection coefficient on the endocardial surface", Physiological Measurement, 2003, vol. 24, pp. 321-335.
Dos Santos et all., "In vivo measurements of heat transfer on the endocardial surface", Physiological Measurement, 2003, vol. 24, pp. 793-804.
Dos Santos, "In vivo measurements of the heat convection coefficient on the endocardial surface", PhD Dissertation, Univ. Texas-Austin, 2003, pp. 1-95.
Eick, Phd, "Factors Influencing Lesion Formation During Radiofrequency Catheter Ablation", Indian Pacing Electrophysiol Journal, Jul.-Sep. 2003, vol. 3(3), pp. 117-128.
Gopalakrishnana, "A Mathematical Model for Irrigated Epicardial Radiofrequency Ablation", Annals of Biomedical Engineering, 2002, vol. 30, pp. 884-893.
Haines, M.D., "Determinants of Lesion Size During Radiofrequency Catheter Ablation: The Role of Electrode-Tissue Contact Pressure and Duration of Energy Delivery", J. Cardiovasc Electrophysiol, Dec. 1991, vol. 2, pp. 509-515.
Heammerich et al., "Thermal Dose versus Temperature as Lesion Boundary Estimate", Short Paper & Presentation, EMBC 2003, Cancun, Sep. 2003.
Jain, "An Experimental and Numerical Analysis of the Spatiotemporal Behavior of Radiofrequency Ablation", PhD Dissertation, Duke University, 1999, pp. 1-225.
Lai et al., "Lesion Size Estimator of Cardiac Radiofrequency Ablation at Different Common Locations With Different Tip Temperatures", IEEE Transactions on Biomedical Engineering, Oct. 2004, vol. 51 (10), pp. 1859-1864.
Shimoike, MD et al., "Experimental Ablation Study Using a New Long Linear Probe in Isolated Porcine Hearts", Japanese Heart Journal, 1999, vol. 40, pp. 189-197.
Tangwongsan et al., "In Vivo Measurement of Swine Endocardial Convective Heat Transfer Coefficient", Aug. 2004, vol. 51(8), pp. 1478-1486.
Tangwongsan, "Measurement of in vivo Endocardial and Hepatic Convective Heat Transfer Coefficient", PhD Dissertation, Univ. of Wisconsin-Madison, Aug. 2003.
Tsai et al., "In Vitro Measurement of Myocardial Impedivity Anisotropy With a Miniature Rectangular Tube", IEEE Transactions on Biomedical Engineering, Apr. 2003, vol. 50(4), pp. 528-532.
Tsai et al., "Noncontact RF Ablation Creates Larger Myocardial Lesions", PACE, Apr. 1999 (Part II), vol. 22, p. 822.
Tsai et al., "Dependence of Apparent Resistance of Four-Electrode Probes on Insertion Depth", IEEE Transactions on Biomedical Engineering, 2000, vol. 47(1), pp. 41-48.
Tsai et al., "Measurement of Swine Aortic Resistivity", Proceedings—19th Int'l Conference—IEEE/EMBS, Oct. 30-Nov. 2, 1997, Chicago, Il, USA, pp. 152-153.
Tsai et al., "In-Vivo Measurement of Swine Myocardial Resistivity", IEEE Transactions on Biomedical Engineering, May 2002, vol. 49(5), pp. 472-483.
Tsai et al., "Error Analysis of Tissue Resistivity Measurement", IEEE Transactions on Biomedical Engineering, May 2002, vol. 49(5), pp. 484-494.
Tsai, "Measurement of in vivo and in vitro Swine Myocardial Resistivity", PhD Dissertation, Univ. of Wisconsin-Madison, May 2001, pp. 1-137.
Tungjitkusolmun et al., "Modeling Bipolar Phase-Shifted Multielectrode Catheter Ablation", IEEE Transactions on Biomedical Engineering, Jan. 2002, vol. 49(1), pp. 10-17.
Tungjitkusolmun et al., "Finite Element Analyses of Uniform Current Density Electrodes for Radio-Frequency Cardiac Ablation", IEEE Transactions on Biomedical Engineering, Jan. 2000, vol. 47(1), pp. 32-40.
Tungjitkusolmun et al., "Using Ansys for Three-Dimensional Electrical-Thermal Models for Radio-Frequency Catheter Ablation", Proceedings—19th Int'l Conference—IEEE/EMBS, Oct. 30-Nov. 2, 1997, Chicago, IL, USA, pp. 161-164.
Tungjitkusolmun et al., "Guidelines for Predicting Lesion Size at Common Endocardial Locations During Radio-Frequency Ablation", IEEE Transactions on Biomedical Engineering, Feb. 2001, vol. 48(2), pp. 194-201.

(56) References Cited

OTHER PUBLICATIONS

Tungjitkusolmun et al., "Thermal-electrical finite element modelling for radio frequency cardiac ablation: effects of changes in myocardial properties", Med., & Bio. Engineering & Computing, 2000, vol. 38, pp. 562-568.
Tungjitkusolmun, "Finite Element Modeling of Radio-Frequency Cardiac and Hepatic Ablation", PhD Dissertation, Univ. of Wisconsin-Madison, Aug. 2000, pp. 1-213.
Woo et al., "Needle Electrode Design for RF Ablation of Ventricular Myocardium", PACE, Apr. 1999 (Part II), vol. 22, p. 846.
Woo et al., "A New Catheter Design Using Needle Electrode for Subendocardial RF Ablation of Ventricular Muscles" Finite Element Analysis and in vitro Experiments, IEEE Transactions on Biomedical Engineering, Jan. 2000, vol. 47(1), pp. 23-31.
Vorperian, RF ablation talk by Vicken R. Vorperian, M.D. with images from many sources, Power Point Presentation (10 MB), Apr. 2000.
Zhang et al., "Noncontact Radio-Frequency Ablation for Obtaining Deeper Lesions", IEEE Transactions on Biomedical Engineering, Feb. 2003, vol. 50(2), pp. 218-223.
Zilinski, Examination of Heat Shocked Bovine Myocardium via Histological Assay, BME 699 course paper, 2000.
36$^{th}$ Annual Scientific Session, Heart Rhythm Society, May 13, 2015, Poster Session PO01-47.
European Search Report dated Dec. 1, 2016 for EP Application No. 16179762.6, 8 pages.

\* cited by examiner

ESTIMATION OF LESION SIZE

CROSS-REFERENCE TO RELATED APPLICATION

This application claims the benefit of U.S. Provisional Patent Application 62/193,179, filed Jul. 16, 2015, which is incorporated herein by reference.

FIELD OF THE INVENTION

The present invention relates generally to ablation of cardiac tissue, and specifically to estimation of the size of a lesion formed during the ablation.

BACKGROUND OF THE INVENTION

The description herein relates to producing a lesion in tissue, typically tissue that is part of the heart of a patient undergoing a cardiac procedure. To produce the lesion a catheter is inserted so that it contacts the tissue, and electromagnetic radiofrequency (RF) energy is injected from a catheter electrode into the tissue, causing ablation and production of a lesion.

Many relations for determining the size of the lesion have been proposed, and one of these relations is considered here. Those having ordinary skill in the art will be aware of other relations. As an example of a relation, the size S of the lesion is assumed to be proportional to a product of the force F applied by the catheter to the tissue, the electromagnetic power P dissipated during the ablation procedure, and the time T of the procedure. (Although the relation involves power P, the relation to lesion size is related to RF Generator Output Current (I), based on the following equation: $P = G \cdot I^2$, where G is a constant. This equation applies to all the following discussion.) Thus, an estimate of the size S of the lesion according to this assumption is given by equation (1):

$$S = K \cdot F \cdot P \cdot T \quad (1)$$

where K is a constant of proportionality and $P = G \cdot I^2$, where I is the RF Generator Output Current.

As is apparent from equation (1), an estimate of the size of a lesion given by the equation is linearly proportional to F, to P, and to T, since in the equation each of these variables is raised to the power of one. I.e., from equation (1) size S is a linear function of F, of P, and of T.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:
ablating tissue for a time period;
measuring a contact force applied during the time period;
measuring a power used during the time period;
and
ceasing ablating the tissue when a desired size of a lesion produced in the tissue, as estimated using an integral over the time period of a product of the contact force raised to a first non-unity exponent and the power raised to a second non-unity exponent, is reached.

In a disclosed embodiment the first non-unity exponent has a value in a range of 0.6-0.8.

In a further disclosed embodiment the second non-unity exponent has a value in a range of 1.4-1.8.

In an alternative embodiment the size includes a volume of the lesion.

In a further alternative embodiment the size includes a depth of the lesion.

In a yet further alternative embodiment the size includes a diameter of the lesion.

Measuring the power may consist of measuring a current generating the power.

There is further provided, according to an embodiment of the present invention, apparatus, including:
a probe configured to ablate tissue for a time period; and
a processor configured to:
measure a contact force applied by the probe during the time period,
measure a power used for ablating the tissue during the time period, and
cease ablating the tissue when a desired size of a lesion produced in the tissue, as estimated using an integral over the time period of a product of the contact force raised to a first non-unity exponent and the power raised to a second non-unity exponent, is reached.

The present disclosure will be more fully understood from the following detailed description of the embodiments thereof, taken together with the drawings, in which:

DETAILED DESCRIPTION OF EMBODIMENTS

Overview

Figure 1:
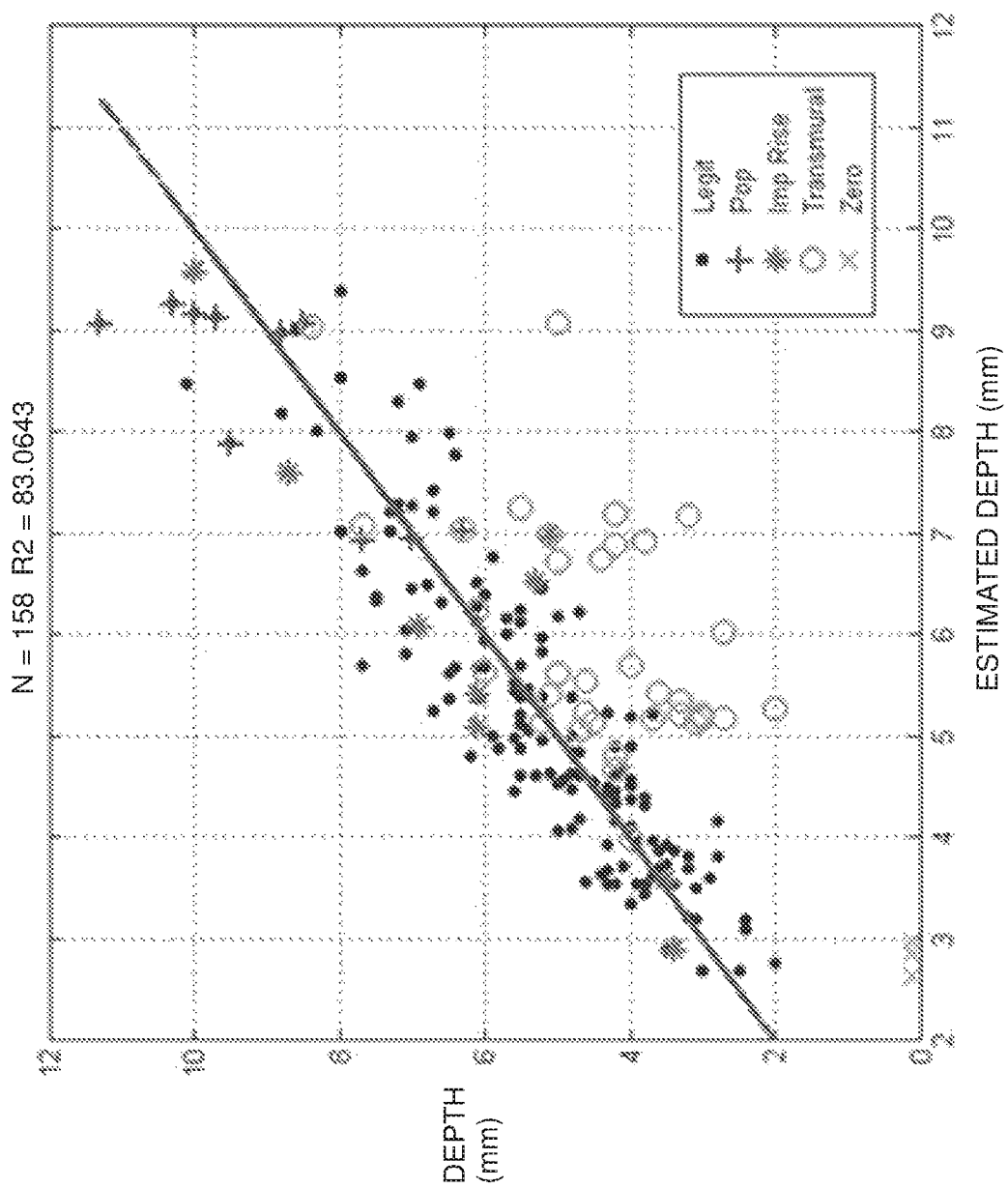
FIG. 1 is a graph of measured lesion depth vs. estimated lesion depth, according to an embodiment of the present invention.

The inventors have found that estimates given by equation (1), as well as similar relations, are inexact, and have found that the relationship between lesion size and F, P, and T is in fact highly non-linear. Following this observation, a process has been developed for making a more exact estimate of the size of a lesion, from the values of F, P, and T. The inventors have found, and have verified by experiment, that a more exact estimate of lesion size is given by finding an integral over time of an expression comprising non-linear functions of F, P, and T. The estimate may be applied during ablation of tissue separately to estimating the volume of the lesion, the depth of the lesion, and/or the diameter of the lesion produced in the tissue, so as to cease the ablation when a desired size is reached.

In an embodiment of the present invention, tissue is ablated for a time period. During the time period a contact force applied to the tissue by a probe performing the ablation is measured, and the power is also measured. An estimate of the size of the lesion produced is made using an integral over the time period of a product of the contact force raised to a first non-unity exponent and the power raised to a second non-unity exponent. When the estimated size reaches a desired size, the ablation stops.

DETAILED DESCRIPTION

The inventors have found that equation (2) gives a very good estimate of the volume of a lesion that is produced by ablation of tissue with electromagnetic power.

$$V(T) = C \int_0^T CF^\alpha(t) P^\beta(t) dt \quad (2)$$

where V(T) is the volume of the lesion produced by ablation over a time period T;

C is a constant of proportionality;

CF(t) is a value of the instantaneous contact force, at a time t, applied to the tissue during the ablation;

P(t) is a value of the instantaneous power, at a time t, dissipated during the ablation; and $\alpha$, $\beta$ are numerical exponents having values not equal to 1 (unity).

Since, as stated above, the power P can be expressed in terms of the current I flowing as $P = G \cdot I^2$, equation (2) can also be written as:

$$V(T) = C \cdot G \int_0^T CF^\alpha(t) I^{2\beta}(t) dt \quad (2a)$$

where G is a constant, and where I(t) is a value of the instantaneous current flowing at time t.

In the following description of results the units used for each of the variables in evaluating equations (2) and (2a) are assumed, by way of example, to be as in Table I.

TABLE I

| Variable | Units |
|---|---|
| V(T) | mm³ |
| CF(t) | g (grams) |
| P(t) | W (watts) |
| I(t) | A (amps) |
| t, T | s (seconds) |
| C | $\frac{mm^3}{g \cdot W \cdot s}$ |
| $\alpha$, $\beta$ | dimensionless |

Those having ordinary skill in the art will be able to adapt the results for units different from those of Table I.

Alternative equations to equation (2) and ((2a) are equations (3) and (4);

$$Depth^\gamma(T) = C \int_0^T CF^\alpha(t) P^\beta(t) dt = C \cdot G \int_0^T CF^\alpha(t) I^{2\beta}(t) dt \quad (3)$$

where each of the terms are as defined above with respect to equations (2) and (2a), and where Depth is the depth of the lesion in mm; and $\gamma$ is a numerical exponent not equal to 1 (unity).

$$Diam^\delta(T) = C \int_0^T CF^\alpha(t) P^\beta(t) dt = C \cdot G \int_0^T CF^\alpha(t) I^{2\beta}(t) dt \quad (4)$$

where each of the terms are as defined above with respect to equations (2) and (2a), and where Diam is the diameter of the lesion in mm; and $\delta$ is a numerical exponent not equal to unity.

The inventors have found that equations (3) and (4) give very good estimates respectively of the depth and diameter of a lesion, so that taken together or separately, equations (2), (2a), (3), (4) give very good estimates of a size of the lesion.

Approximations to the Equations Equations (2), (2a), (3), and (4) may be approximated by assuming that CF or P or I do not vary over the time period T. The following description describes approximations for equation (3), but those having ordinary skill in the art will be able to apply similar approximations for equations (2) and (4).

For simplicity, in the following description equation (3) assumes that the equation only incorporates the first equality, i.e., that the equation is:

$$Depth^\gamma(T) = C \int_0^T CF^\alpha(t) P^\beta(t) dt \quad (3')$$

Those having ordinary skill in the art will be able to change equation (3') if current I is considered.

If P is assumed to have a fixed value over the time period T of the ablation, then equation (3') can be rewritten:

$$Depth^\gamma(T) = C P^\beta \int_0^T CF^\alpha(t) dt \quad (5)$$

If CF is almost fixed or if $\alpha \approx 1$ then $$\int_0^T CF^\alpha(t) dt \approx ACF^\alpha \cdot R \quad (6)$$

where ACF is an average value of CF over time T.

Substituting equation (6) into equation (5) gives:

$$Depth^\gamma = C \cdot ACF^\alpha \cdot P^\beta \cdot T \quad (7)$$

Values of C, $\alpha$, $\beta$, and $\gamma$

Taking logs of both sides of equation (7) gives:

$$Log(Depth) = \frac{1}{\gamma} Log(C) + \frac{\alpha}{\gamma} Log(ACF) + \frac{\beta}{\gamma} Log(P) + \frac{1}{\gamma} Log(T) \quad (8)$$

The inventors performed 180 ablation sessions to derive values of C, $\alpha$, $\beta$, and $\gamma$ in equation (8). Using results from 158 valid ablations generated in the sessions, the inventors applied linear regression analysis to evaluate C, $\alpha$, $\beta$, and $\gamma$. The regression analysis gave the following results:

$\gamma = 2.78$;

$\alpha = 0.67$;

$\beta = 1.58$;

$C = \frac{1}{503.82}$

Inserting these values into equation (3') gives:

$$Depth(T) = \left[ \frac{1}{503.82} \int_0^T CF^{0.67}(t) P^{1.58}(t) dt \right]^{0.36} \quad (9)$$

FIG. 1 is a graph of measured lesion depth vs. lesion depth estimated from equation (9), according to an embodiment of the present invention. The graph illustrates the good correlation between the values of the estimated lesion depth and the measured values:

In the graph "Transmural" points are where the cardiac tissue was penetrated, "Imp rise" points are where a rise in impedance was observed, "Pop" points are where steam pops occurred during the RF application, and "Legit" are valid points apart from those listed above.

The correlation between the estimated and measured values of depth for the 158 results is very good. A calculated correlation coefficient R for the values gives $R^2=82.9\%$, so that R=0.910.

Appendix II below provides an alternative analysis of the 158 results, and gives the following values for C, $\alpha$, $\beta$, and $\gamma$:

$$\gamma = 2.83;$$
$$\alpha = 0.68;$$
$$\beta = 1.63;$$
$$C = \frac{1}{531.88}.$$

Using these values, equation (3) becomes $$\text{Depth}(T) = \left[\frac{1}{531.88}\int_0^T CF^{0.68}(t)P^{1.63}(t)dt\right]^{0.35} \quad (10)$$

Comparing the results of equation (10) with the measured depth results gives $R^2=83.1\%$, so that R=0.911.

For both sets of values (of C, $\alpha$, $\beta$, and $\gamma$), $$\alpha \approx \frac{2}{3},$$

The inventors believe that $\alpha$ may have a value in the range of 0.6-0.8, and that $\beta$ may have a value in the range of 1.4-1.8.

The integral $\int_0^T CF^\alpha(t)P^\beta(t)dt$ is herein termed an ablation index, and is referred to as $I_{FTP}$ or as FPTI. Thus, $$I_{FTP} = \int_0^T CF^\alpha(t)P^\beta(t)dt \approx \int_0^T CF^{\frac{2}{3}}(t)P^{\frac{3}{2}}(t)dt \quad (11)$$

Figure 2A:
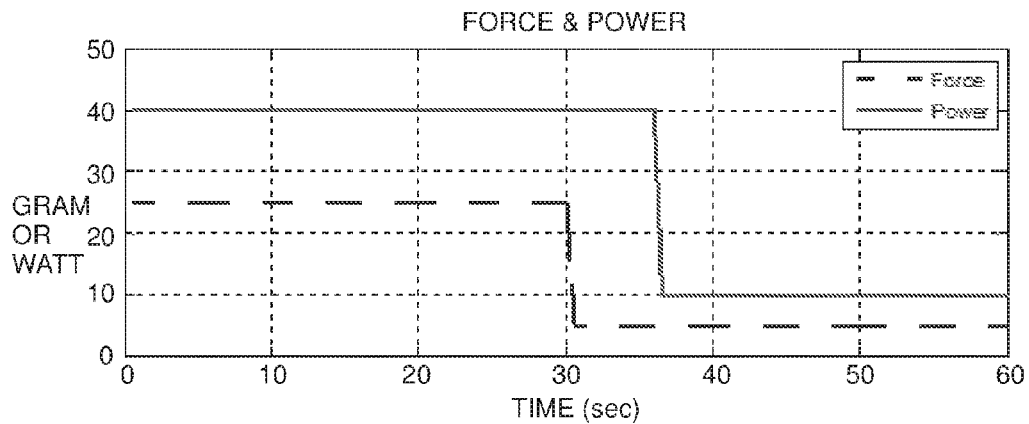
FIGS. 2A, 2B, and 2C are graphs of force, power, depth and an index vs. time, according to an embodiment of the present invention.
Figure 2B:
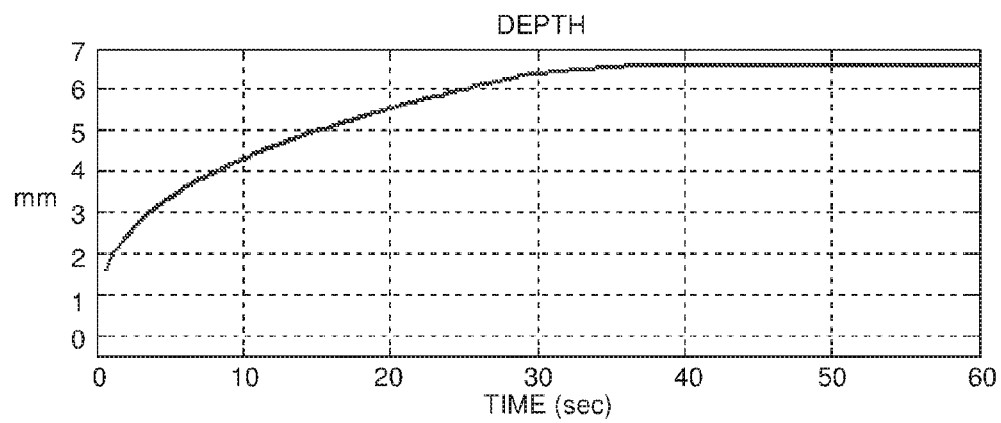
Figure 2C:
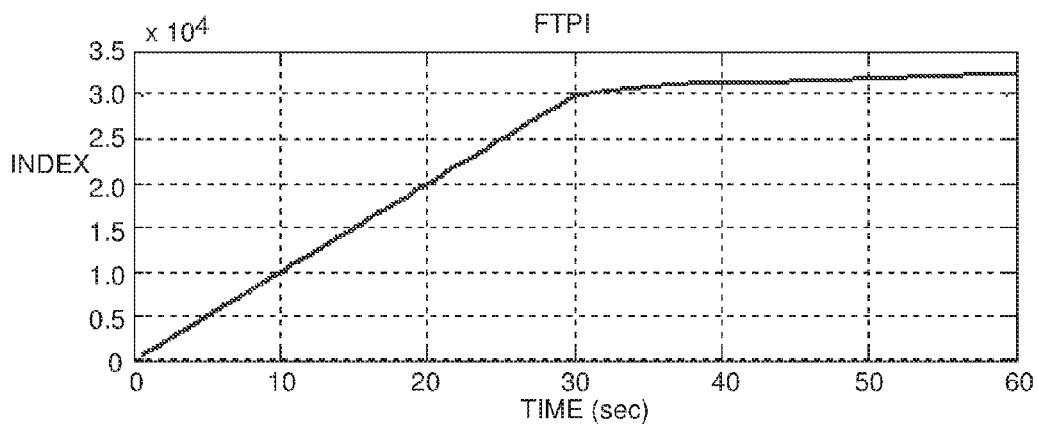

FIGS. 2A, 2B, and 2C are graphs of force, power, depth and FTPI vs. time, according to an embodiment of the present invention. The graphs provide an example of the estimated depth and of the ablation index when both the power and the force change. The graph of depth vs. time shows that the estimated depth is always positive and is always monotonically increasing.

The inventors have determined that for a given type of cardiac structure and a given tissue characteristic the value of the ablation index is a very good, and repeatable, predictor of lesion size. Furthermore, lesion size for a given value of ablation index may be different for different structures and tissue characteristics.

In a retrospective study, of 159 patients, each ablation site was reviewed offline to identify the ablation index for each CPVI (circumferential pulmonary vein isolation) segment according to a 9-segment model around the CPVI circumferences. For example, the median ablation index for segments with adenosine-mediated acute reconnection (ARc) was 293, as compared to the median index for segments without ARc of 342, and for posterior/inferior segments with ARc the median index was significantly lower (286) than for those without ARc (321).

Figure 3:
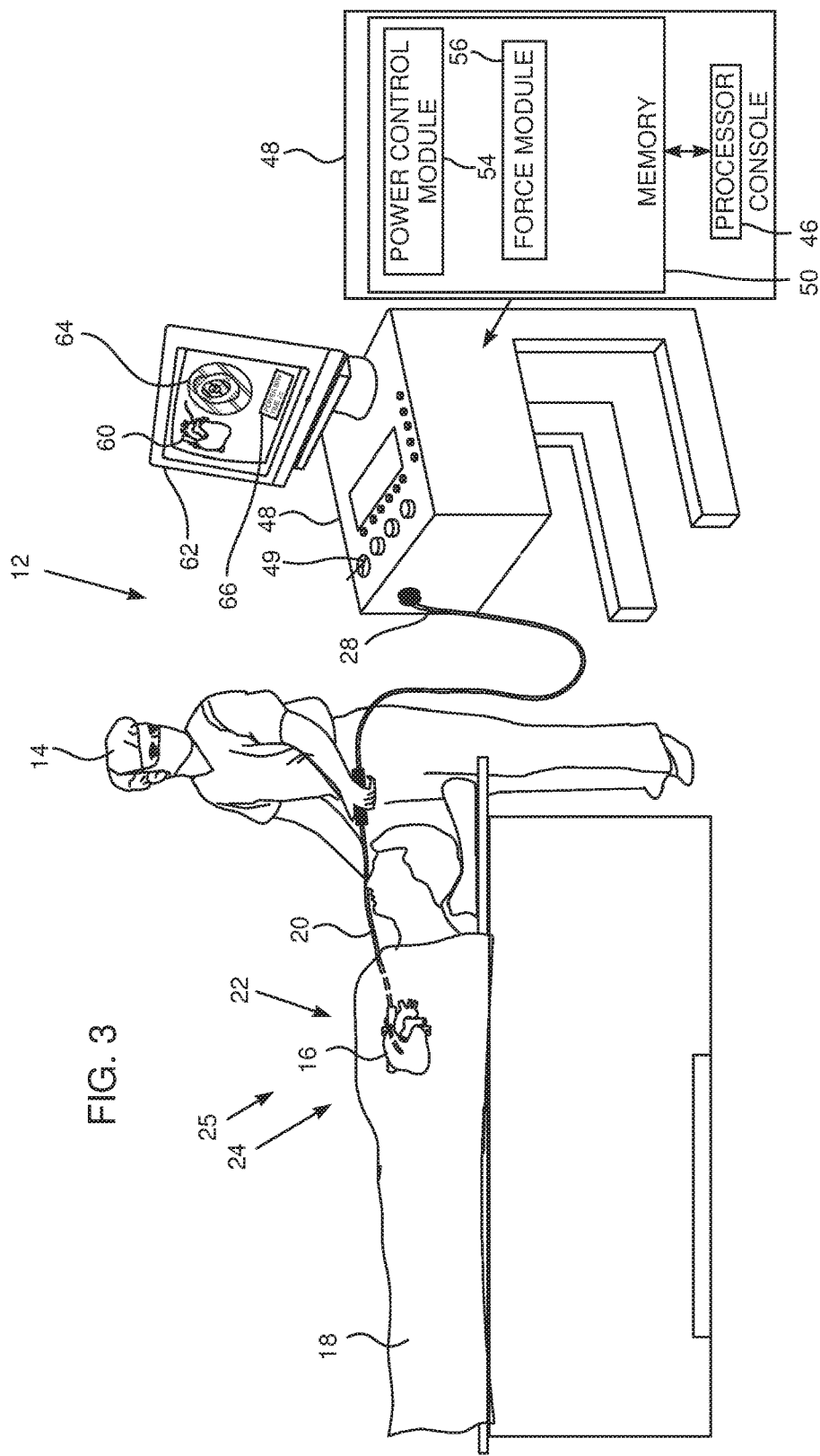
FIG. 3 is a schematic illustration of an ablation procedure being performed by an ablation apparatus, according to an embodiment of the present invention.

FIG. 3 is a schematic illustration of an ablation procedure performed using apparatus 12, according to an embodiment of the present invention. As explained below with reference to the flowchart of FIG. 4, the procedure uses estimates of lesion size that may be derived from one or more of equations (2)-(11).

The procedure is performed by a physician 14, and, by way of example, the procedure in the description herein below is assumed to comprise ablation of a portion of a myocardium 16 of the heart of a human patient 18.

In order to perform the ablation, physician 14 inserts a probe 20 into a lumen of the patient, so that a distal end 22 of the probe enters the heart of the patient. Distal end 22 comprises an electrode 24 mounted on the outside of the distal end, the electrode contacting a location of the myocardium. Distal end 22 also comprises a force sensor 25. Probe 20 has a proximal end 28.

Apparatus 12 is controlled by a system processor 46, which is located in an operating console 48 of the apparatus. Console 48 comprises controls 49 which are used by physician 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62. The progress of the ablation performed with apparatus 12 is typically also displayed on screen 62, as a graphic 64 and/or alphanumeric data 66.

In order to operate apparatus 12, processor 46 communicates with a memory 50, which has a number of modules used by the processor to operate the apparatus. Thus, memory 50 comprises a power control module 54, and a force module 56. Power control module 54 delivers radiofrequency (RF) power to one of electrodes 24, and also measures the instantaneous power P(t) delivered at a time t, typically by measuring the instantaneous current I(t) delivered by the electrode. Force module 56 measures the instantaneous contact force CF(t) at time t, by acquiring and evaluating signals from force sensor 25 in distal end 22. Memory 50 may also comprise other modules, such as a temperature measuring module and an irrigation module. For simplicity such other modules are not described further in this application. The modules of memory 50 may comprise hardware as well as software elements.

Figure 4:
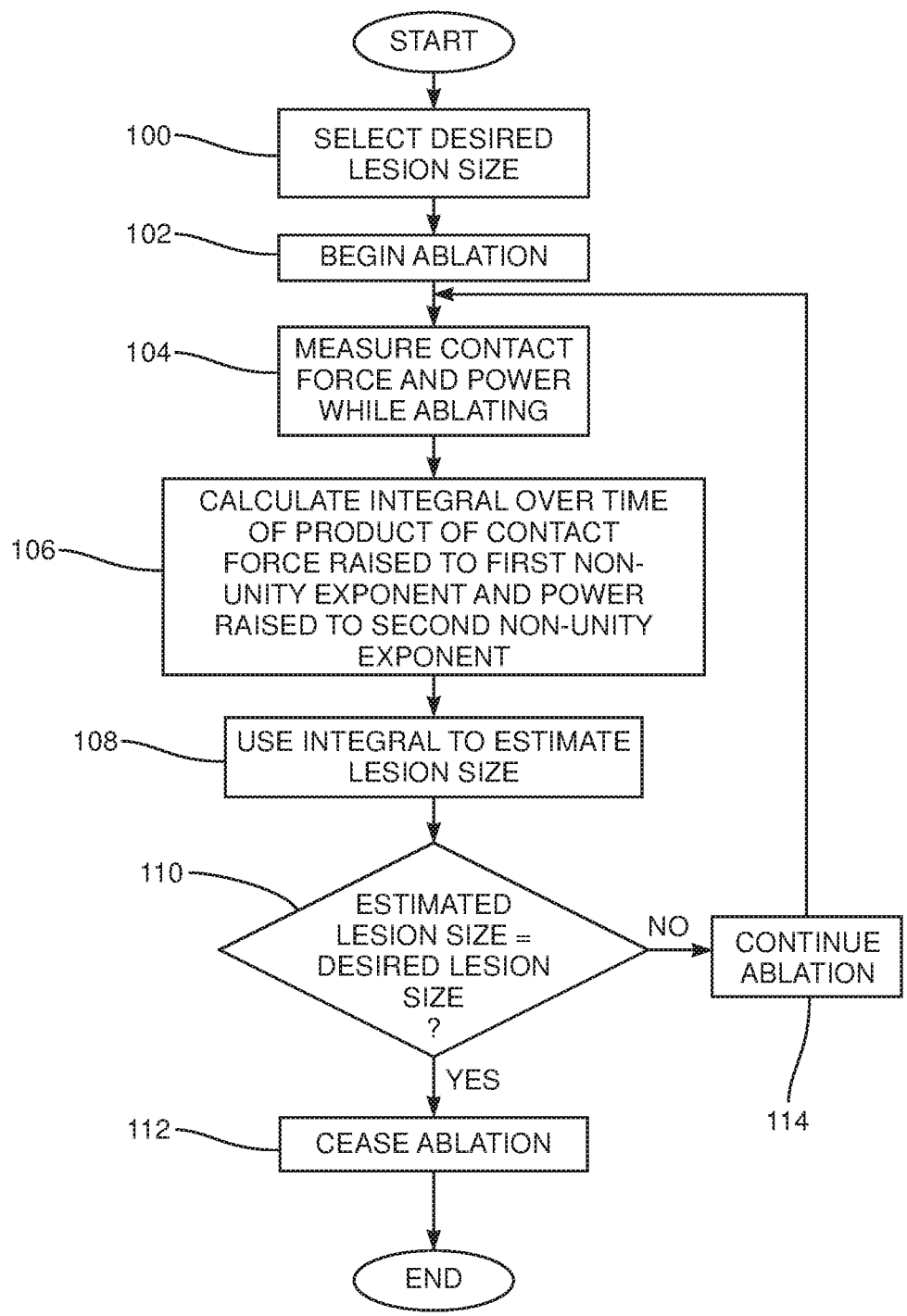
FIG. 4 is a flowchart of steps performed in using the ablation apparatus, according to an embodiment of the present invention.

FIG. 4 is a flowchart of steps performed by physician 14 in using apparatus 12, according to an embodiment of the present invention. In an initial step 100, the physician selects a desired size for the lesion. By way of example, the physician may select a desired depth that is in the range of 1 mm-5 mm. In addition, the physician selects values of C, $\alpha$, $\beta$, and $\gamma$ to be used in an equation for depth estimation to be used, herein assumed to be equation (3). For example, values of C, $\alpha$, $\beta$, and $\gamma$ may be selected to be as given above for equation (9), i.e., $\gamma = 2.78;$ $\alpha = 0.67;$ $\beta = 1.58;$ $C = \frac{1}{503.82}.$ However, the physician may determine, without undue experimentation, other values for C, α, β, and γ, and may use these values.

For clarity, in the remaining steps of the flowchart, equations (9) and (11) are assumed to be used for determining an estimated depth of the lesion.

In a start ablation step 102, the physician uses controls 49 to select a nominal power to be delivered by power control module 54. Typically the power selected is in the range of 10 W to 20 W, although a power outside this range may be selected. After the nominal power has been selected, the physician uses controls 49 to begin the ablation.

In a measuring step 104, as the ablation is being performed, power control module 54 measures the instantaneous power P(t) dissipated by electrode 24, which is typically different from the nominal power. In addition force module 56 measures the instantaneous contact force CF(t) on distal end 22.

In a calculation step 106, as the ablation proceeds processor 46 calculates, on a recurring basis, the value of the integral used in equation (9), i.e., the value of ablation index $I_{FTP}$ in equation (11). In a size estimation step 108, the processor calculates a value of the estimated size, i.e., the estimated depth, using the integral value and equation (9).

In a decision step 110 the processor checks if the estimated size is equal to the desired size. If the decision returns positive, in a final step 112 the processor ceases the ablation. If the decision returns negative the processor, in a continuing ablation step 114 continues to ablate and the flowchart returns to measuring step 104.

The following Appendices provide more detail on aspects of the invention.

Appendix I

In the regression analysis regarding equation (8) the inventors assumed $\int_0^T CF^\alpha(t)dt \approx ACF^\alpha \cdot T$. The assumption was checked using the value of α (=0.67).

A true CF average is given by equation (12):

$$\text{True } CF \text{ average} = \frac{1}{T}\int_0^T CF^{0.67}(t)dt \quad (12)$$

An assumed CF average is given by equation (13):

$$\text{Assumed } CF \text{ average} = \left(\frac{1}{T}\int_0^T CF(t)dt\right)^{0.67} \quad (13)$$

Figure 5:
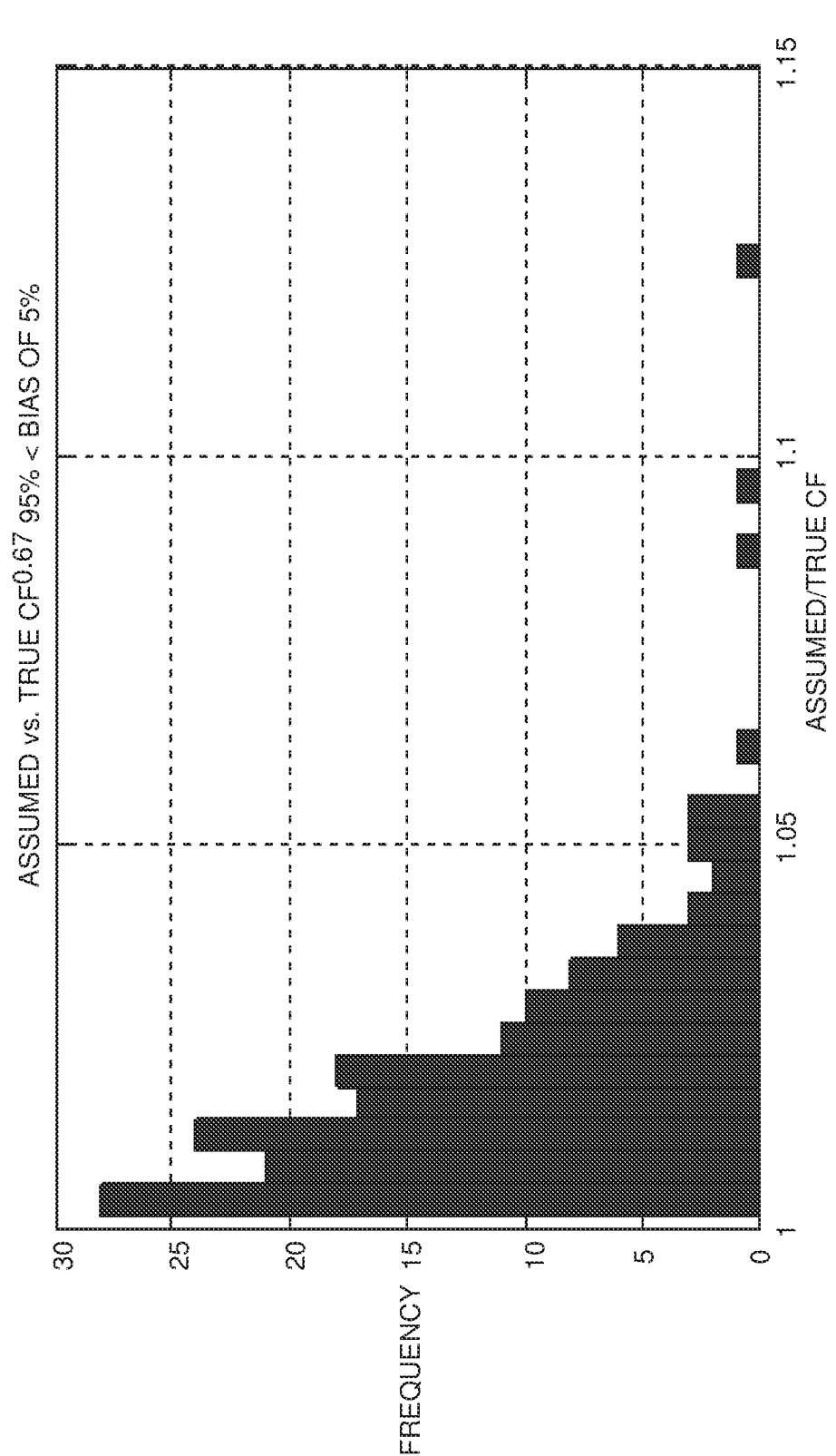
FIG. 5 is a histogram comparing true and assumed average contact forces, according to an embodiment of the present invention.

FIG. 5 is a histogram comparing the true and assumed average contact forces, according to an embodiment of the present invention. The histogram gives the frequencies of the ratio of the two quantities, $$\frac{\text{Assumed } CF \text{ average}}{\text{True } CF \text{ average}},$$

for the 158 ablations studied.

The histogram illustrates that in 95% of the ablations, the deviation between the two quantities is less than 5%, and has an average deviation of 2%. The assumption is thus justified.

Appendix II

An alternative method for analyzing the 158 results estimates an RMS value (given by equation (14) below), and finds values of C, α, β, and γ which minimize the RMS value.

$$\text{RMS} = \sqrt{\sum_{i=1}^{158} ((\text{Log}(\text{Measured } Depth_i) - \text{Log}(\text{Estimated } Depth_i))^2} \quad (14)$$

where $$\text{Estimated } Depth_i = \left[\frac{1}{C}\sum_{t=1}^{N_i} CF_i^\alpha(t)P_i^\beta(t)dt\right]^{\frac{1}{\gamma}}$$

The inventors used the Matlab fminsearch function, using as starting points the values of C, α, β, and γ determined by the regression analysis, i.e., $\gamma_0$=2.78; $\alpha_0$=0.67; $\beta_0$=1.58; $C_0$=1/503.82. The function returned the values $\gamma_{min}$=2.83; $\alpha_{min}$=0.68; $\beta_{min}$=1.63; $C_0$=1/531.88, as used in equation (10) above.

Appendix III

The inventors analyzed the data from the 158 results using Bland-Altman plots, looking for any fixed bias in the measurements. As is known in the art, if the mean value of the differences differs significantly from 0 then a fixed bias is indicated.

A first plot was constructed for all the data, and then four separate plots were constructed for sub-groups of data. The data and the plots are given below.

Inspection of all five sets of data and plots shows that in no case does the mean value differ significantly from 0.

Figure 6:
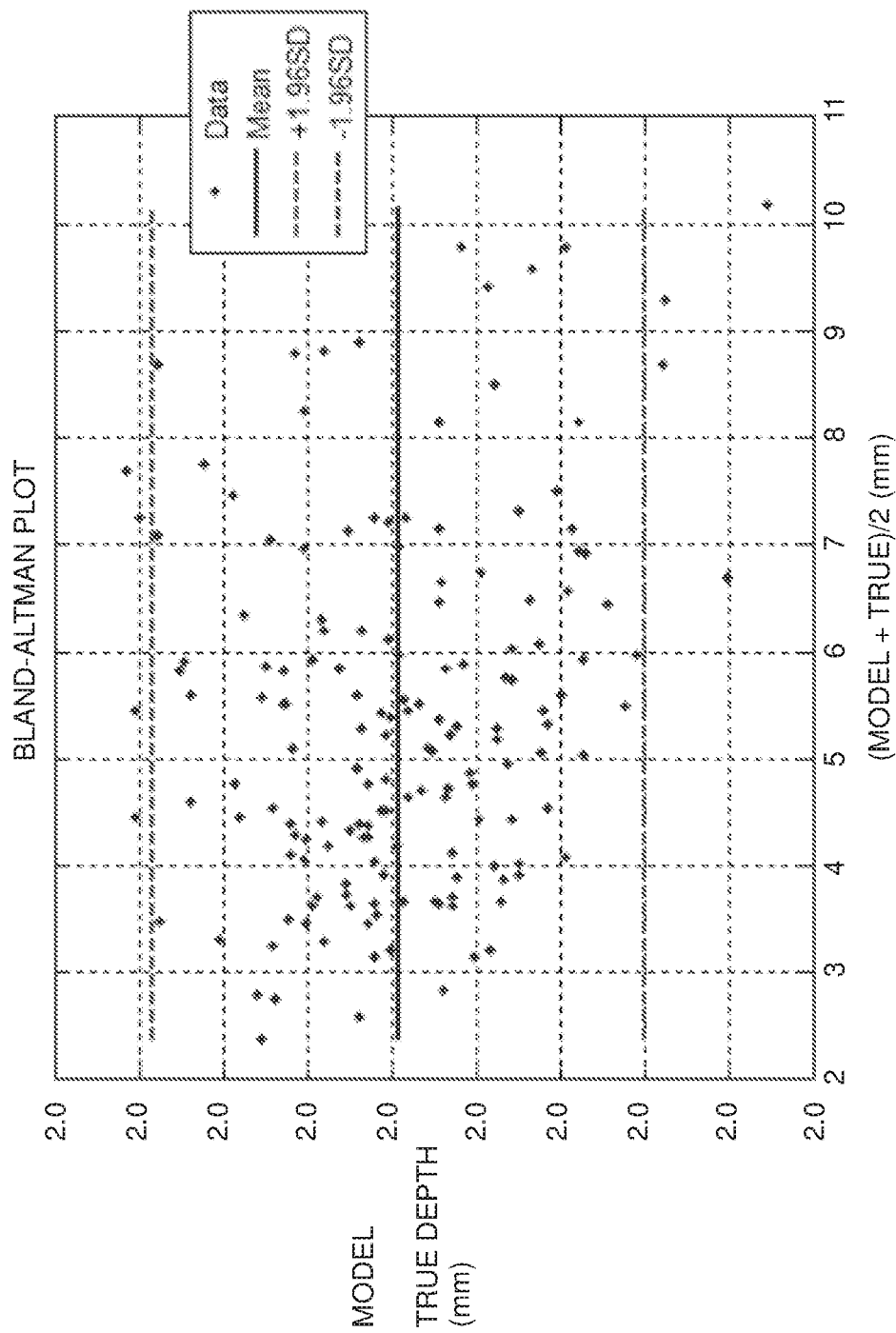
FIGS. 6-10 are Bland-Altman plots for different sets of data, according to an embodiment of the present invention.

FIG. 6 is a Bland-Altman plot for the following first set of data, according to an embodiment of the present invention.

1. All data N=158

| Min | 20.00% | 50.00% | 80.00% | Max | Mean | STD |
|---|---|---|---|---|---|---|
| −2.23 | −0.69 | 0.01 | 0.58 | 1.58 | −0.05 | 0.74 |

Figure 7:
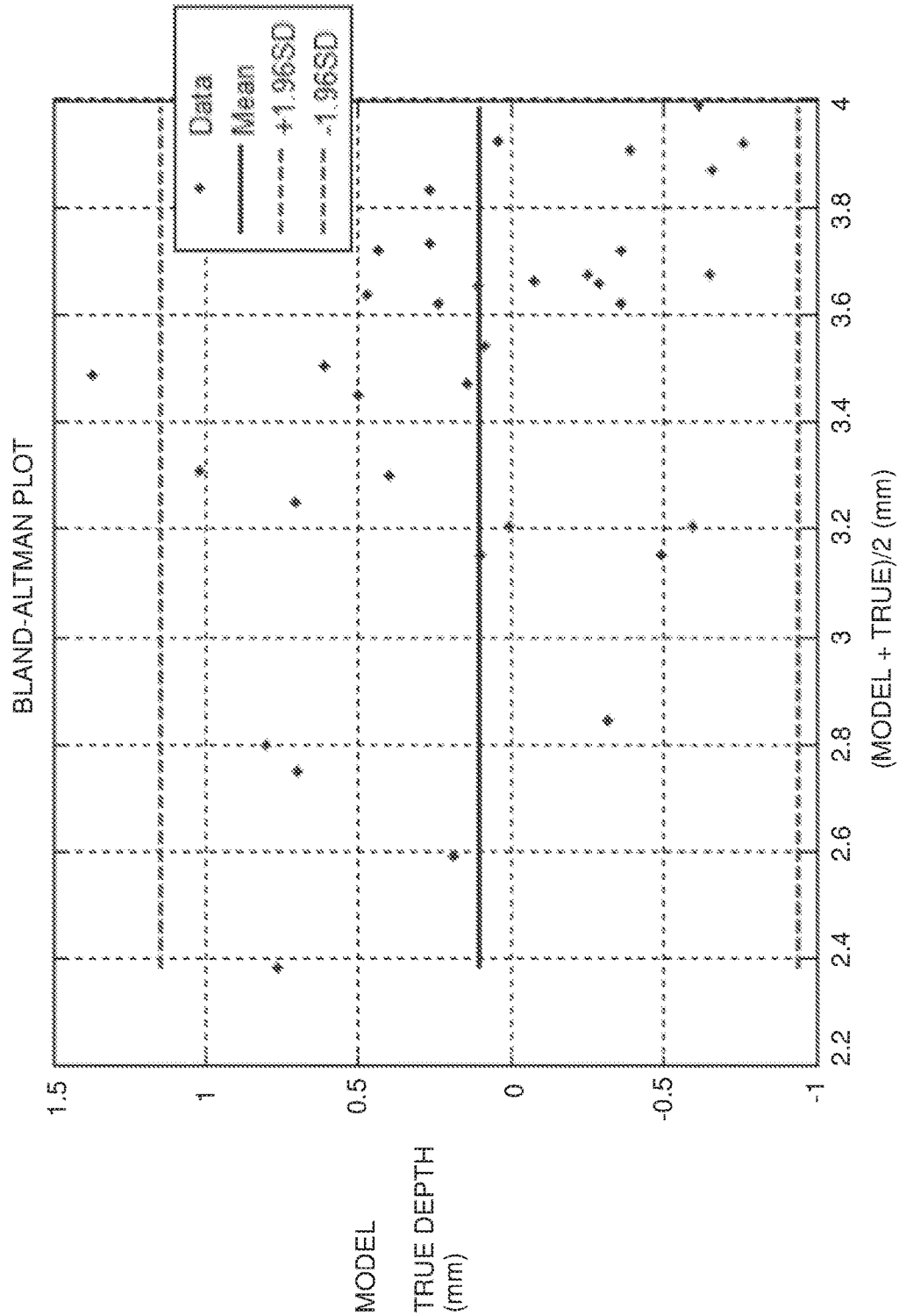

FIG. 7 is a Bland-Altman plot for the following second set of data, according to an embodiment of the present invention.

2. (depth+model)/2=2-4 mm N=34

| Min | 20.00% | 50.00% | 80.00% | Max | Mean | STD |
|---|---|---|---|---|---|---|
| −0.76 | −0.38 | 0.10 | 0.58 | 1.37 | 0.10 | 0.53 |

Figure 8:
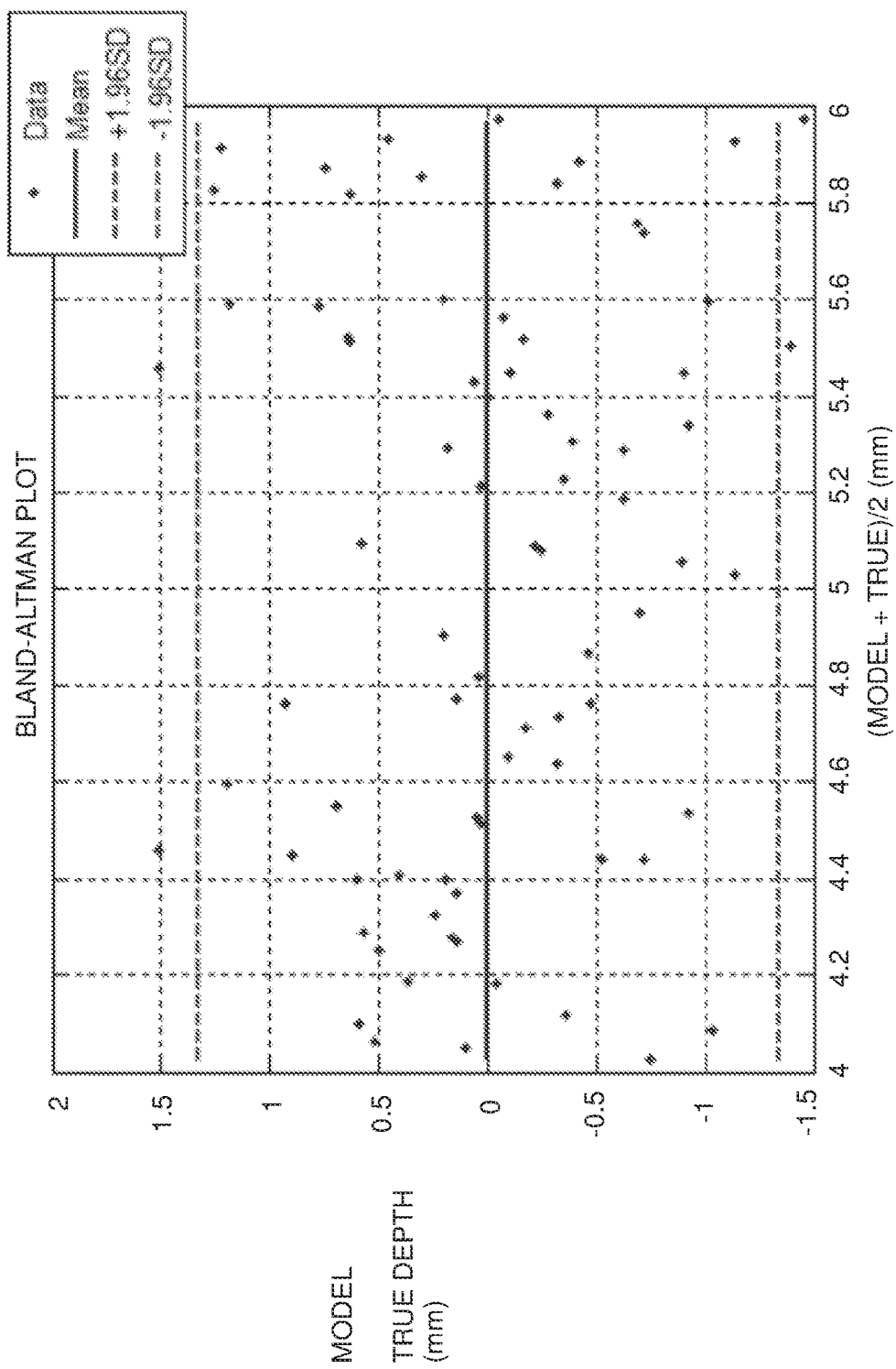

FIG. 8 is a Bland-Altman plot for the following third set of data, according to an embodiment of the present invention.

3. (depth+model)/2=4-6 mm N=77

| Min | 20.00% | 50.00% | 80.00% | Max | Mean | STD |
|---|---|---|---|---|---|---|
| −1.45 | −0.63 | 0.03 | 0.60 | 1.52 | 0.00 | 0.68 |

Figure 9:
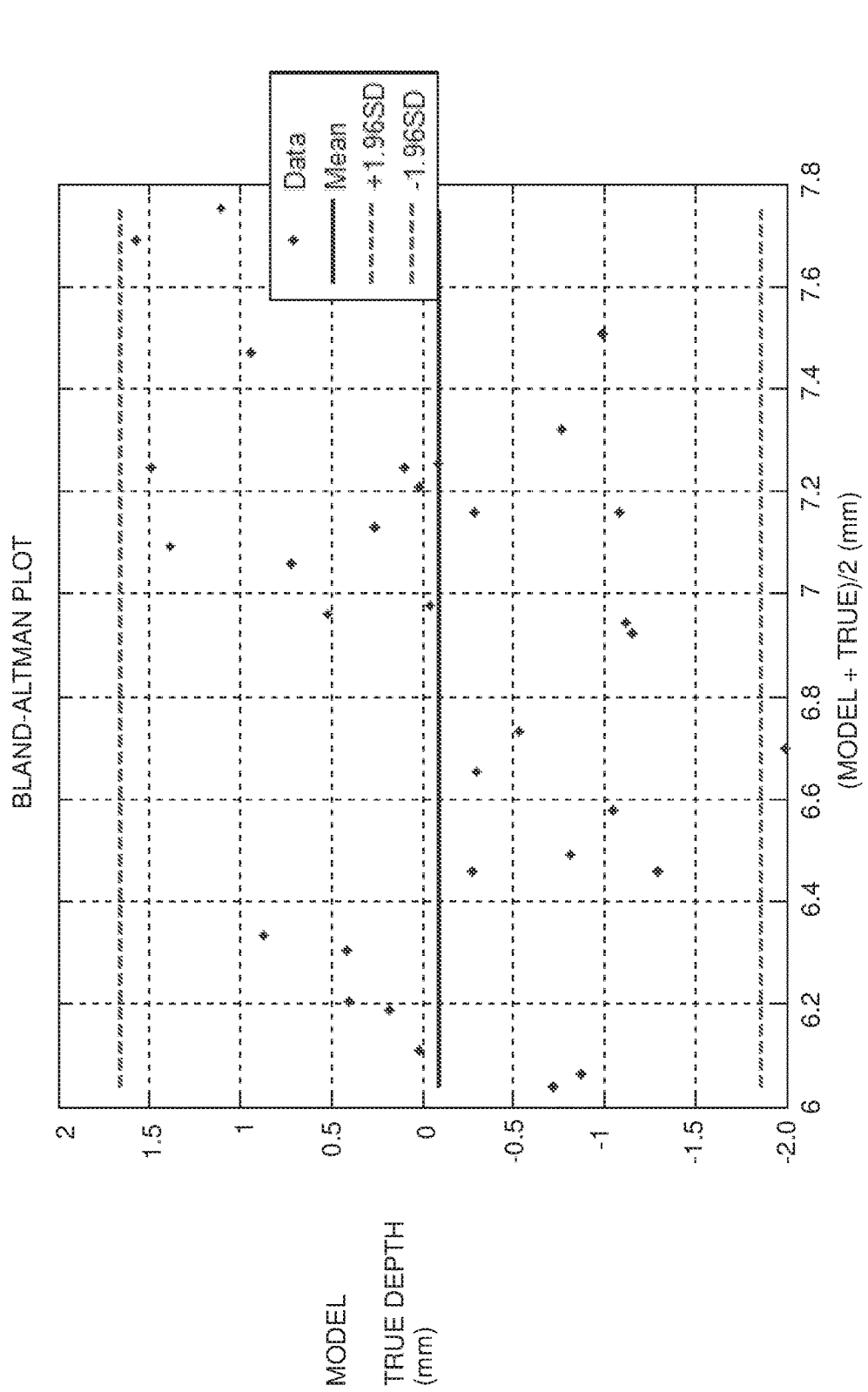

FIG. 9 is a Bland-Altman plot for the following fourth set of data, according to an embodiment of the present invention.

4. (depth+model)/2=6-8 mm N=32

| Min | 20.00% | 50.00% | 80.00% | Max | Mean | STD |
|---|---|---|---|---|---|---|
| −2.00 | −0.99 | −0.07 | 0.73 | 1.58 | −0.10 | 0.90 |

Figure 10:
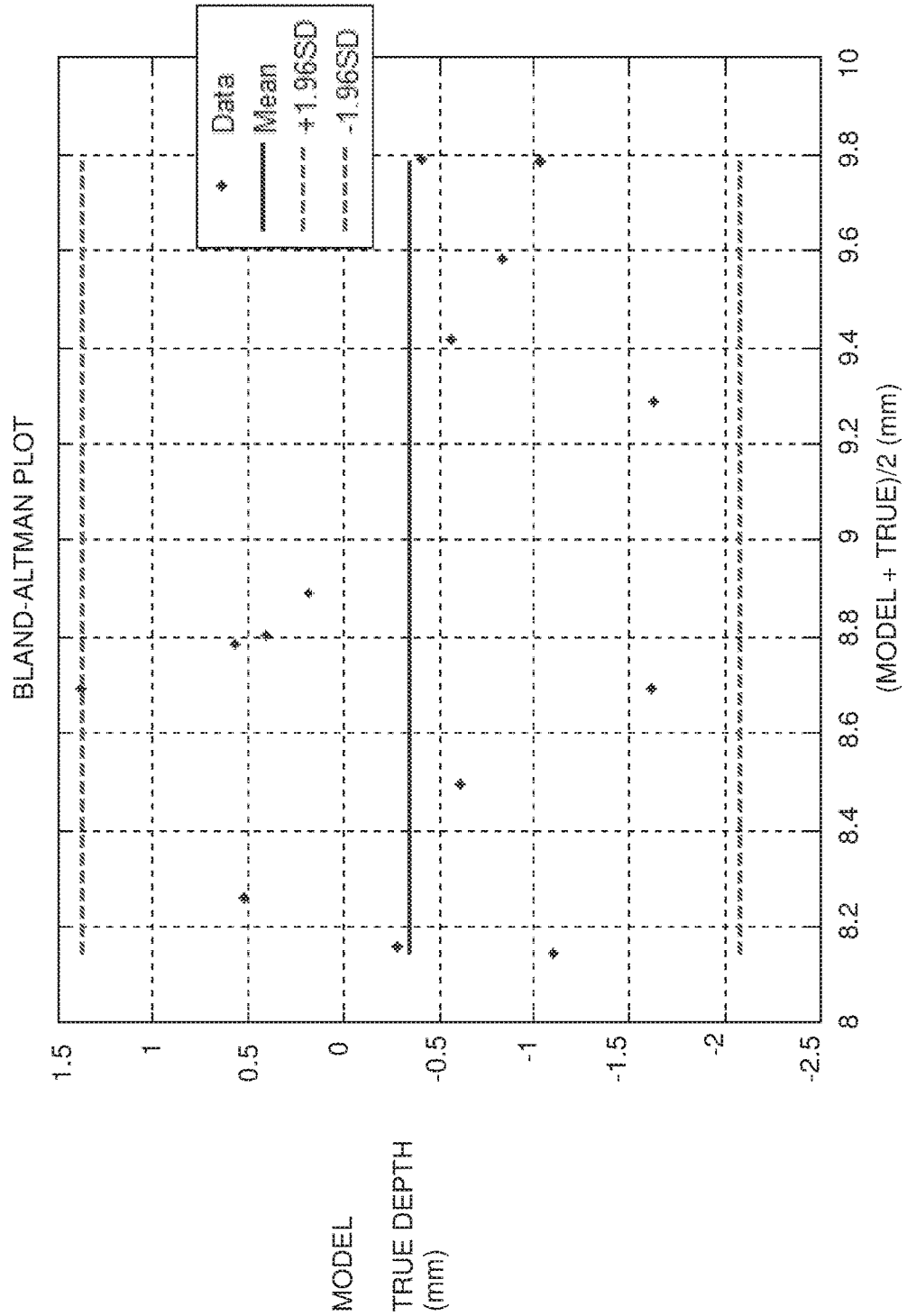

FIG. 10 is a Bland-Altman plot for the following fifth set of data, according to an embodiment of the present invention.

5. (depth+model)/2=8-10 mm N=14

| Min | 20.00% | 50.00% | 80.00% | Max | Mean | STD |
|---|---|---|---|---|---|---|
| −1.63 | −1.08 | −0.49 | 0.49 | 1.38 | −0.36 | 0.88 |

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
a probe configured to ablate tissue for a time period; and
a processor configured to:
measure an instantaneous contact force applied by the probe during the time period,
measure an instantaneous power used for ablating the tissue during the time period, and
cease ablating the tissue when a desired size of a lesion produced in the tissue, as estimated using an integral over the time period of a product of the instantaneous contact force raised to a first non-unity exponent and the instantaneous power raised to a second non-unity exponent, is reached, wherein the first non-unity exponent and the second non-unity exponent are determined through linear regression.

2. The apparatus according to claim 1, wherein the first non-unity exponent has a value in a range of 0.6-0.8.

3. The apparatus according to claim 1, wherein the second non-unity exponent has a value in a range of 1.4-1.8.

4. The apparatus according to claim 1, wherein the desired size comprises a volume of the lesion.

5. The apparatus according to claim 1, wherein the desired size comprises a depth of the lesion.

6. The apparatus according to claim 1, wherein the desired size comprises a diameter of the lesion.

7. The apparatus according to claim 1, wherein measuring the instantaneous power comprises measuring a current generating the instantaneous power.

8. A method, comprising:
ablating tissue for a time period with a probe;
measuring an instantaneous contact force applied by the probe during the time period;
measuring an instantaneous power used for ablating the tissue during the time period; and
ceasing ablating the tissue when a desired size of a lesion produced in the tissue, as estimated using an integral over the time period of a product of the instantaneous contact force raised to a first non-unity exponent and the instantaneous power raised to a second non-unity exponent, is reached, wherein the first non-unity exponent and the second non-unity exponent are determined through linear regression.

9. The method according to claim 8, wherein the first non-unity exponent has a value in a range of 0.6-0.8.

10. The method according to claim 8, wherein the second non-unity exponent has a value in a range of 1.4-1.8.

11. The method according to claim 8, wherein the desired size comprises a volume of the lesion.

12. The method according to claim 8, wherein the desired size comprises a depth of the lesion.

13. The method according to claim 8, wherein the desired size comprises a diameter of the lesion.

14. The method according to claim 8, wherein measuring the instantaneous power comprises measuring a current generating the instantaneous power.

* * * * *